United States Patent
Voges

(10) Patent No.: US 6,443,146 B1
(45) Date of Patent: *Sep. 3, 2002

(54) PIEZO INHALER

(75) Inventor: Robert Martin Voges, Solana Beach, CA (US)

(73) Assignee: Ponwell Enterprises Limited, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/513,279

(22) Filed: Feb. 24, 2000

Related U.S. Application Data

(63) Continuation of application No. 09/256,144, filed on Feb. 24, 1999, now Pat. No. 6,196,218.

(51) Int. Cl.$^7$ ............................................. A61M 11/00
(52) U.S. Cl. ............................ 128/200.14; 128/200.23
(58) Field of Search .................. 128/200.12–200.14, 128/200.18, 200.16, 200.21, 200.24, 202.21, 203.12, 203.14, 203.26, 203.27; 239/338, 102.1, 102.2

(56) References Cited

U.S. PATENT DOCUMENTS

| | | | | | |
|---|---|---|---|---|---|
| 3,863,630 A | * | 2/1975 | Cavallo | ................... | 128/145.6 |
| 4,294,407 A | * | 10/1981 | Reichl et al. | ................ | 239/102 |
| 4,301,093 A | * | 11/1981 | Eck | ........................ | 128/200.16 |
| 4,632,311 A | * | 12/1986 | Nakane et al. | ............ | 239/102.1 |
| 4,877,989 A | * | 10/1989 | Drews et al. | ........... | 128/200.16 |
| 5,038,769 A | * | 8/1991 | Krauser | ................... | 128/203.27 |
| 5,134,993 A | * | 8/1992 | Van Der Linden et al. | ...... | 128/200.14 |
| 5,152,456 A | * | 10/1992 | Ross et al. | .............. | 128/200.16 |
| 5,186,164 A | * | 2/1993 | Raghuprasad | .......... | 128/200.14 |
| 5,261,601 A | * | 11/1993 | Ross et al. | .............. | 128/200.16 |
| 5,452,711 A | * | 9/1995 | Gault | ..................... | 128/200.16 |
| 5,485,828 A | * | 1/1996 | Hauser | ................... | 128/200.16 |
| 5,487,378 A | * | 1/1996 | Robertson et al. | ...... | 128/200.16 |
| 5,522,386 A | * | 6/1996 | Lloyd et al. | ............ | 128/203.26 |
| 5,529,055 A | * | 6/1996 | Gueret | ................... | 128/200.16 |
| 5,601,235 A | * | 2/1997 | Booker et al. | ........... | 239/102.2 |
| 5,694,919 A | * | 12/1997 | Rubsamen et al. | .... | 128/200.14 |
| 5,724,957 A | * | 3/1998 | Rubsamen et al. | .... | 128/200.16 |
| 5,823,428 A | * | 10/1998 | Humberstone et al. | .. | 239/102.2 |
| 5,829,434 A | * | 11/1998 | Ambrosio et al. | ..... | 128/203.15 |
| 5,881,716 A | * | 3/1999 | Wirch et al. | ................. | 128/200 |
| 5,894,841 A | * | 4/1999 | Voges | ..................... | 128/203.12 |
| 5,970,974 A | * | 10/1999 | Van Der Linden et al. | ...... | 128/200.16 |
| 6,062,212 A | * | 5/2000 | Davison et al. | ......... | 128/200.16 |
| 6,131,570 A | * | 10/2000 | Schuster et al. | ........ | 128/203.26 |
| 6,196,218 B1 | * | 3/2001 | Voges | ..................... | 128/200.14 |

FOREIGN PATENT DOCUMENTS

| | | |
|---|---|---|
| DE | 205820 | 11/1984 |
| DE | 3908909 A1 | 9/1990 |
| WO | WO 93/11866 | 6/1993 |

* cited by examiner

Primary Examiner—John G. Weiss
Assistant Examiner—Teena Mitchell
(74) Attorney, Agent, or Firm—Marsh Fischmann & Breyfogle LLP

(57) ABSTRACT

An inhaler provides a controlled delivery of an inhalant and includes an inhaler housing and a mouthpiece coupled to the inhaler housing. A piezoelectric dispenser-head is coupled to the inhaler housing and configured to be coupled to the dispensing chamber. The piezoelectric dispenser-head includes an array of dispensing channels and an array of dispensing nozzles. The array of dispensing channels are formed with actuatable walls made at least partially of a piezoelectric material. Application of an electric field to selected side walls reduces a volume in an associated channel and creates a pressure pulse of flowable substance in the associated channel through a dispensing nozzle.

51 Claims, 5 Drawing Sheets

PIEZO INHALER

RELATED APPLICATIONS

This patent application is a continuation of and claims priority from U.S. patent application Ser. No. 09/256,144, filed on Feb. 24, 1999, and entitled "Piezo Inhaler," now U.S. Pat. No. 6,196,218 which issued on Mar. 6, 2001, the entire disclosure of which is incorporated in its entirety herein, and further claims priority from: 1) U.S. patent application Ser. No. 08/578,707, filed on Dec. 28, 1995, and entitled "Dispenser," now U.S. Pat. No. 5,894,841 which issued on Apr. 20, 1999; 2) PCT Application No. PCT/AU94/00355, filed on Jun. 28, 1994, and entitled "Dispenser," now abandoned; 3) Australian Patent Application No. PM1709, filed Oct. 8, 1993; 4) Australian Patent Application No. PM0925, filed Aug. 31, 1993; 6) Australian Patent Application No. PL9769, filed Jul. 2, 1993; and 5) Australian Patent Application No. PL9673, filed Jun. 29, 1993.

BACKGROUND OF THE INVENTION

1. Field of the Invention

This invention relates to an inhaler, more particularly to an inhaler with a piezoelectric dispenser-head.

2. Description of Related Art

There are currently three main methods for drug delivery via the respiratory tract, namely metered dose inhalers, dry powder inhalers, and nebulizers.

Metered dose inhalers ("MDI") are widely used in the management of asthma. The MDI comprises a drug packaged with a propellant in a pressurized aerosol container can having a valve which releases a volumetric metered dose of aerosol upon actuation. These inhalers are portable, small, and convenient to carry but deliver a dose which varies in quantity, delivery speed, and droplet size distribution as the vapor pressure of the propellant varies. The propellant pressure varies with temperature and decreases progressively as the content becomes depleted so that the range in dose variation may be substantial. Incomplete evaporation of the propellant may cause "sticking" and localized concentration of drug droplets at an impact area, and this in turn can cause undesirable side effects. For example bronchosteroids can cause local immuno-suppression and local fungal infection while local concentration of bronchodilator can lead to swallowing, with unwanted systemic affects. In addition, the use of an MDI requires a degree of synchronization between manual valve actuation and inhalation which many users find difficult.

Dry powder inhalers ("DPI") devices rely upon a burst of inspired air to fluidize and draw a dose of an active powder into the bronchial tract. While this avoids the synchronization problem of the MDI, DPI's are sensitive to humidity and may provoke asthma attacks in some individuals sensitive to inhaled powder. Moreover, because the force of inspiration varies from person to person, the dose administered varies.

Nebulizers generate an aerosol by atomizing a liquid in a carrier gas stream and require a continuous gas compressor or bulky supply of compressed gas. In general, the droplet size of the aerosol is a function of carrier gas pressure and velocity and hence cannot be easily varied independently of concentration of the active substance in the gas stream. Inhalation reduces the pressure at the nebulizer nozzle and thus dosage and particle size are also influenced by the duration and strength of each breath. Most nebulizers operate continuously during inhalation and exhalation but special control systems can be employed to meter the aerosolized gas flow from the nebulizer to a holding chamber from which the user may draw a charge.

In general the precision of dose delivery of each of these devices is less accurate than desirable and restricts their use to drugs which have broad dosage tolerance. In each case delivery of the active agent to the intended application site is overly dependent on user technique and is variable from dose to dose and person to person. Not only is an improved delivery system required to optimize current nasal and pulmonary therapies utilizing locally acting drugs but there has long been recognized a potential for the administration of many additional local and systemic drugs if a more satisfactory means of delivery were available. Medical advances suggest that pulmonary delivery of drugs such as peptides, proteins and analgesics might be of considerable advantage compared with conventional oral or injection delivery means. For example it has been suggested that insulin for diabetics may be delivered via the pulmonary route if a suitable means of delivery were available. The deposition of drug particles on lung tissue is a function of size, shape and density of particles or droplets. For many drugs, control of one or more of these factors along with precise dose or dose rate control would be desirable. However, at the present time no means of drug delivery is available which adequately meets such requirements.

Many attempts have been made to provide a cigarette substitute which provides nicotine by inhalation but which avoids the need for combustion of tobacco. Provision of a cigarette substitute involves complexities additional to those involved in the administration of a therapeutic agent. Although it is relatively easy to administer nicotine (for example in tablet form, via transdermal patches and the like), such forms do not satisfy habitual smokers because they do not satisfy important complex physiological and psychological affinities acquired by habitual smokers of combustible cigarettes.

In an attempt to provide an acceptable alternative, many cigarette substitutes have been proposed which provide nicotine on inhalation without combustion of tobacco. Conceptually, such devices are less harmful to the inhaler than smoking, avoiding the hazards of; passive smoking among bystanders, and the fire hazard and environmental problems associated with cigarette smoking. However, despite these major advantages, no device so far proposed has met with consumer acceptance.

Early cigarette substitutes employed a porous carrier impregnated with a liquid nicotine containing composition through which an air stream could be drawn to volatilize nicotine. This approach yielded insufficient nicotine per puff, suffered from a tendency for the carrier to dry out and delivered a variable amount of nicotine per puff, depending on factors such as air temperature, humidity, lung capacity of the user and amount of liquid composition remaining in the carrier.

Subsequent devices delivered nicotine from a pressurized aerosol container from which nicotine can be released by mechanical valve actuator. In one such device the valve is microprocessor controlled to limit the frequency and duration of actuation. However, the dose delivered varies with the vapor pressure of aerosol remaining in the container as well as with duration of valve actuation. The disposable pressure container, aerosol valve, and CFC propellant add considerably to active substance cost. These devices share the disadvantages of MDI devices previously discussed.

In yet other devices a nicotine containing substance is heated to vaporize an amount of nicotine which is then available for inhalation. The amount of nicotine delivered by such devices is difficult to control and is temperature dependant. In one such device a plurality of nicotine-containing pellets may be heated sequentially so that each liberates a predetermined dose. However, in that case, the dose is fixed during pellet manufacture, particle size of the aerosol is uncontrolled, and temperature of the inhaled air cannot be varied independently of dose.

Factors such as the quantity of nicotine per puff, the temperature of the puff, the draw, the presence and size distribution of flavor particles in the puff and like factors are of considerable importance in satisfying habitual smokers. The various alternatives proposed to date have simply proved unacceptable to most smokers.

To date no device has provided a satisfactory means of adjusting both the quantity of nicotine delivered in each puff in response to user demand and/or maintaining adequate precision and accuracy in the dose quantum metered out. Further the devices have failed adequately to mimic the sensations obtained during smoking.

SUMMARY OF THE INVENTION

An object of the invention is to provide an inhaler.

Another object of the invention is to provide an inhaler that delivers a variety of different medicaments.

Yet another object of the invention is to provide an inhaler that provides controlled delivery of a medicament.

Still another object of the invention is to provide an inhaler that can be substituted for a cigarette.

A further object of the invention is to provide an inhaler that includes a piezoelectric dispenser-head.

A further object of the invention is to provide an inhaler that includes a piezoelectric dispenser-head and an array of dispensing channels.

These and other objects of the invention achieve an inhaler that dispenses a flowable substance. The inhaler includes an inhaler housing and a mouthpiece coupled to the inhaler housing. A piezoelectric dispenser-head is coupled to the inhaler housing and configured to be coupled to the dispensing chamber. The piezoelectric dispenser-head includes an array of channels and an array of dispensing nozzles. The array of channels are formed with actuatable walls made at least partially of a piezoelectric material. Application of an electric field to selected side walls reduces a volume in an associated channel and creates a pressure pulse of flowable substance in the associated channel through a dispensing nozzle.

DETAILED DESCRIPTION

Figure 1:
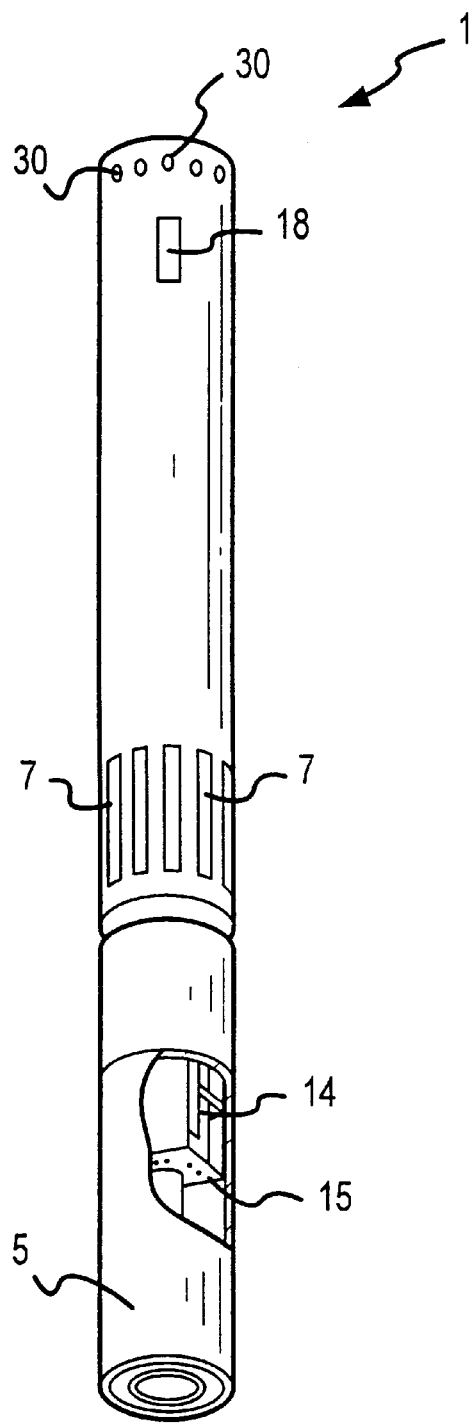
FIG. 1 is a schematic part sectional perspective view of one embodiment of an inhaler (cigarette substitute) according to the invention.
Figure 2A:
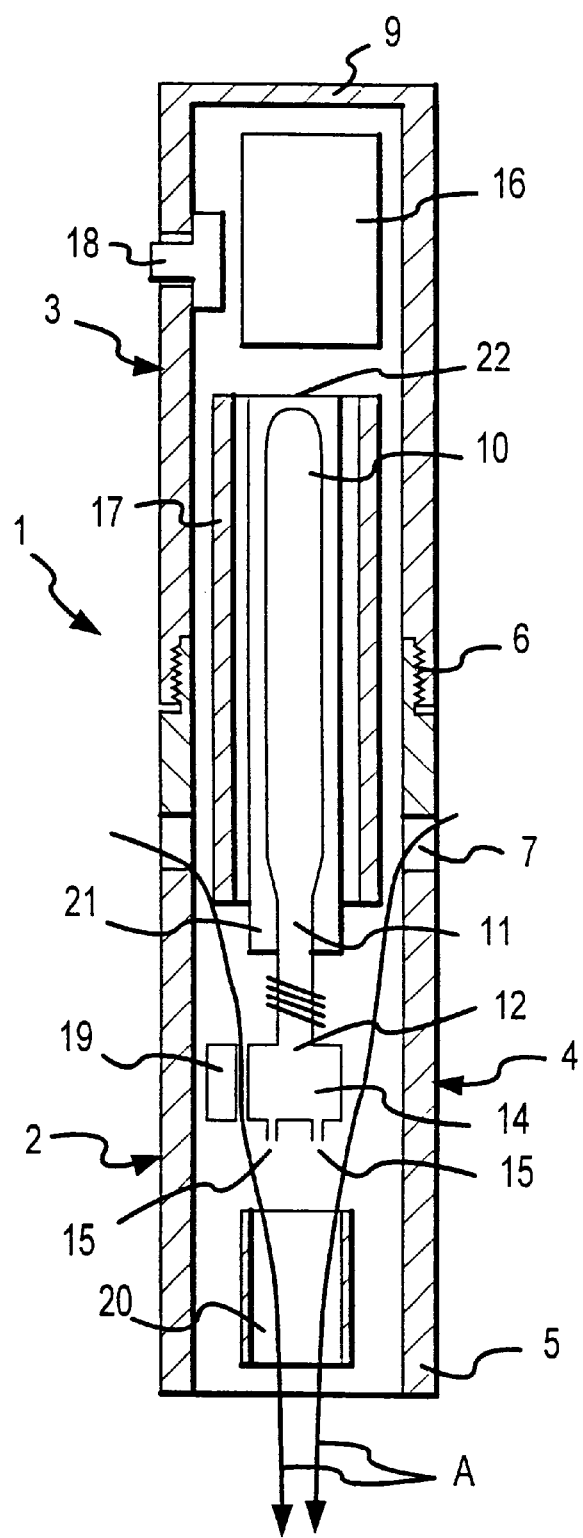
FIG. 2(a) is a schematic section in an axial plane of the inhaler of FIG. 1.
Figure 2B:
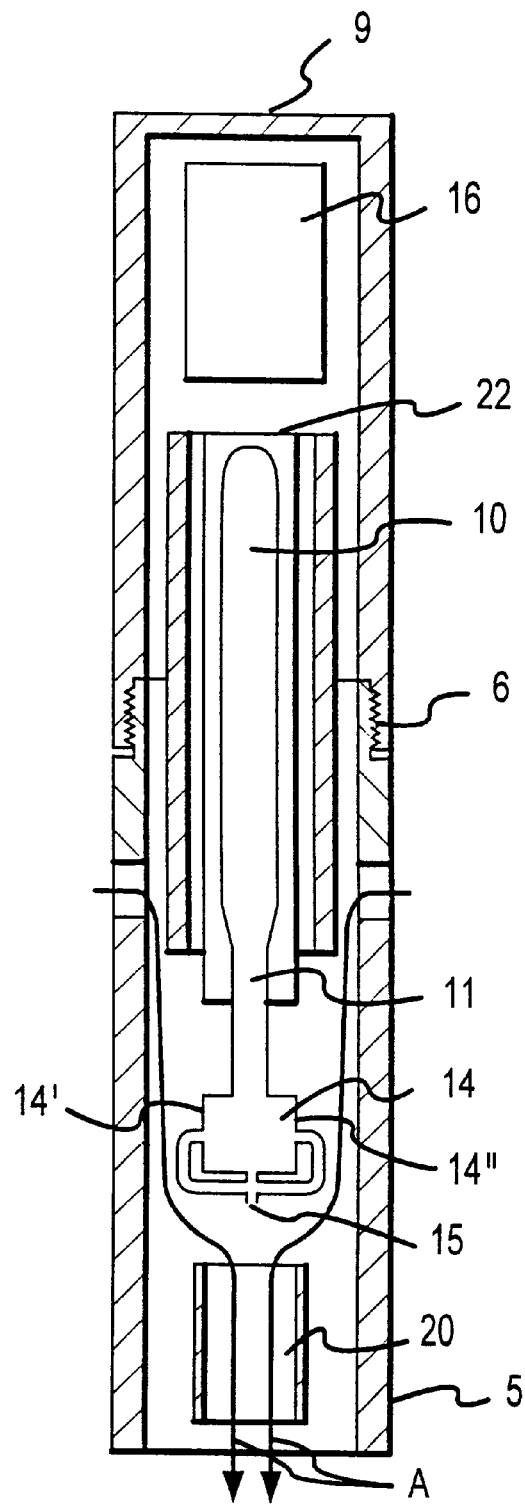
FIG. 2(b) illustrates in a schematic section another embodiment of the inhaler of FIG. 1 that includes a dispensing head with first and second sides, first and second dispensing channels, each of which is coupled to a dispensing nozzle.
Figure 3A:
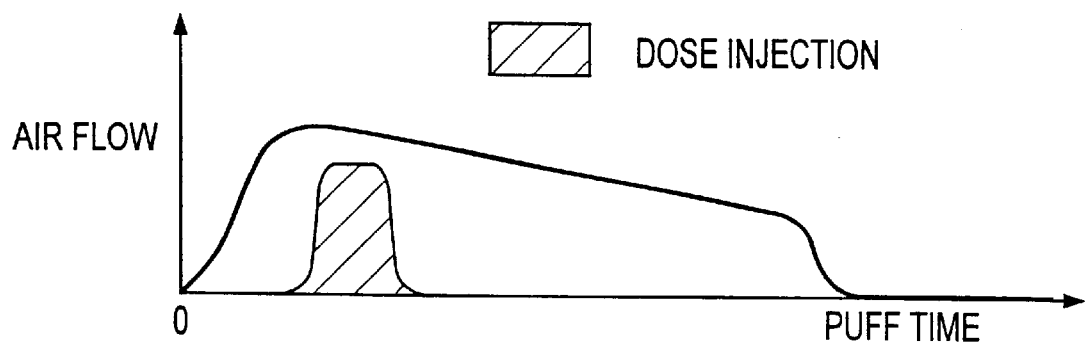
FIGS. 3A, 3B and 3C are graphs showing the dispensation of an active ingredient (hatched) as a function of inhalation time in use of the embodiment of FIG. 1.
Figure 3B:
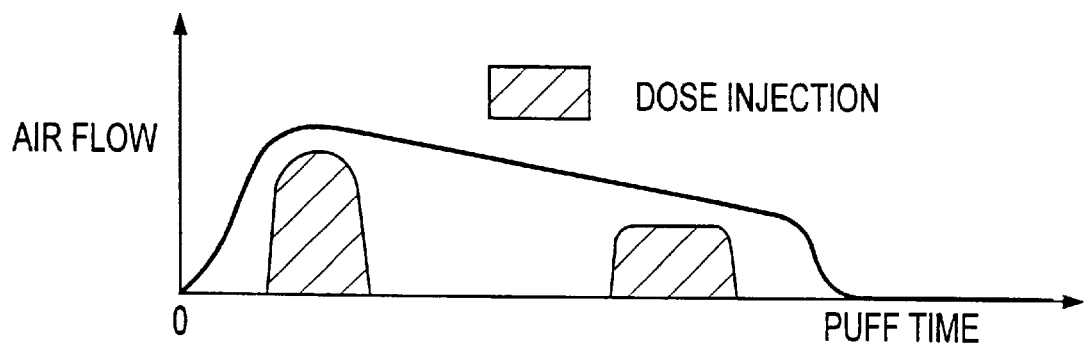
Figure 3C:
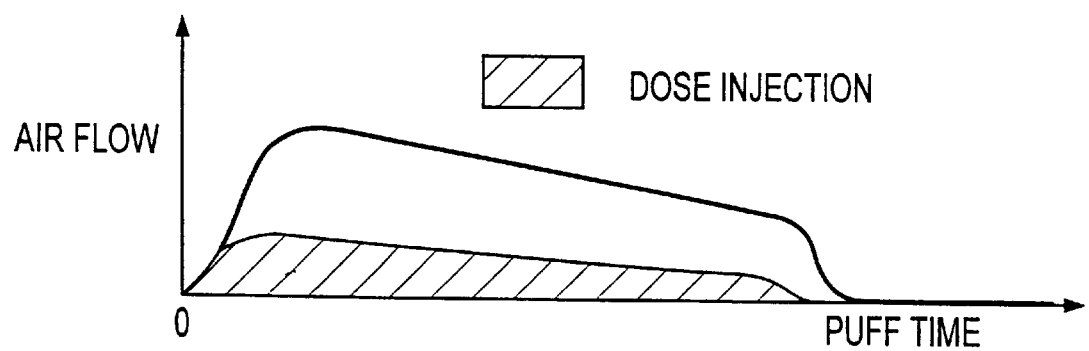

With reference to FIGS. 1, 2(a) and 2(b) there is shown a first embodiment of the invention consisting of a dispenser (hereafter referred to as an "inhaler") that can include a cigarette-shaped hollow tubular body 1 with connected body parts 2, 3. Body part 2 has a side wall 4, a mouthpiece 5 at or adjacent one end and a threaded other end 6. A plurality of axially extending slots 7 penetrate side wall 4. Body part 3 is screw threaded at one end for connection with threaded end 6 of body part 2. Body part 3 is closed or constricted at the end 9 remote from mouthpiece 5.

Nicotine in a suitable solvent (for example water) or other flowable substance is provided in a container 10 which is adapted by means of a spigot shaped outlet and coupling 11, for fluid connection to an inlet port 12 of dispenser-head 14. The dispenser head 14 draws flowable substance from the inlet port 12 and moves it to the droplet dispensing nozzles 15. In one embodiment, dispenser-head 14 is a piezoelectric dispenser-head 14 with one or more droplet dispensing nozzles 15. In another embodiment, dispenser head 14 includes first and second sides 14' and 14" each with a respective dispensing channel that are coupled to dispensing nozzle 15 (FIG. 2(b)). Dispenser-head 14 is controlled by a controller 16. Suitable controllers include but are not limited to electronic and microelectronic circuits and sensors, and the like. In one embodiment dispenser head 14 and controller 16 as well as other electrically-powered parts are energized by means of a hollow cylindrical battery 17 via an on-off switch 18 extending through side wall 4 and operable by the user. When a user inhales at mouthpiece 5, a stream of air "A" is drawn into body 1 via slots 7, through body part 2, and mouthpiece 5 into the user's lungs. Slots 7 may be provided with a damper or the like (not illustrated) to control airflow or the device may be provided with a porous plug to control airflow ("draw") on inhalation at mouthpiece 5. A sensor 19 detects a change in pressure or airflow in the device due to inhalation or suction at mouthpiece 5 and issues an actuation signal via cables (not illustrated) to controller 16. Controller 16 responds to the actuation signal by issuing an output signal or signals via cables (not illustrated) to dispenser-head 14 according to pre-programmed parameters or algorithms as hereinafter described. The output or "dose" signal is, or includes, a set of "eject" signals for example a train of voltage pulses. Dispenser-head 14 responds to the output signal or signals by issuing a plurality of droplets of flowable substance dispensing nozzles 15 of dispenser head 14. The flowable substance issues from dispenser-head 14 as a fine spray of droplets which are entrained in the inhalation airflow from slots 7 towards mouthpiece 5. The spray typically comprises fine droplets which tend to vaporize in the airflow. Optionally, heating means 20 are provided. In that case the combination of air with droplets may be brought into thermally conductive contact with heating means 20 prior to leaving mouthpiece 5. This not only produces a sensation on inhalation similar to that obtained by smoking a combustible cigarette, but also serves to enhance the vaporization of active substance droplets in the gas stream reducing droplet size.

In the embodiment illustrated in FIGS. 1 and 2, the flowable substance container 10 is a collapsible bladder which is housed within a protective hollow cylindrical cartridge 21 having an air vent 22. However other forms of container (for example a cylinder fitted with a piston) could be used. Cartridge 21 is optional and serves to shield container 10. Container 10 is disposable or replaceable and may be adapted for fluid communication with inlet port 12 of dispenser-head 14 by means of a threaded, bayonet, or other suitably sealing connection.

Optionally, battery 17 may be of annular form and adapted to sleeve cartridge 21 to save space. The battery 17 is designed to provide sufficient electrical energy to operate the inhaler. When inhaler is not in use there is a saving of energy. Heating means 20 may be infrared heating plates or elements, resistance elements or the like.

Controller 16 desirably comprises a programmable logic circuit for example a microprocessor together with associated electronic memory, clocks, power supply, sensors and the like and is programmed to control the quantity of flowable substance delivered by the inhaler upon inhalation, subject to predetermined criteria.

In normal operation of the inhaler a drop of pressure, or an increase in airflow, at mouthpiece 5 is detected by sensor 19 which issues a signal indicative of inhalation ("actuation" signal) to controller 16 (via cables not illustrated). Controller 16 responds by issuing a "dose" signal to dispenser-head 14 resulting in a spray of droplets from the inhaler.

The "dose" signal typically comprises a predetermined set of droplet "eject" signals which causes one or more dispensing nozzles 15 of dispenser-head 14 to eject a predetermined number of droplets. The dose signal may, for example, be a train of pulses (each pulse being a droplet eject signal) directed serially to one of the channels of the dispenser-head 14, or may be a sequence of pulses directed in parallel to a number of channels in the dispenser-head 14. Since the volume of a droplet issued from a selected dispensing nozzles 15 is predetermined for a given flowable substance and orifice, and the number of droplets ejected is controlled by the "dose" signal, the total volume of flowable substance ejected in response to the "actuation" signal is precisely determined.

Controller 16 controls the pulse spacing, pulse width, and pulse frequency of the "dose" signal as well as the number of pulses or droplet "eject" signals and therefore determines the time interval during which droplets enter the inhalation air stream i.e. the dose rate. The number of droplets issued and/or the droplet issue frequency may be altered by changing data stored in the memory of the controller 16. Controller 16 may also be programmed to address specific channels of the dispenser-head 14 so as to emit droplets from selected droplet dispensing nozzles 15 which may differ one from another for example in respect of diameter or orientation.

Controller 16 may also be programmed to provide a time delay between receipt of an "actuation in that the body is of rectangular cross-section and in that of the shape and arrangement of components differs.

Figure 4:
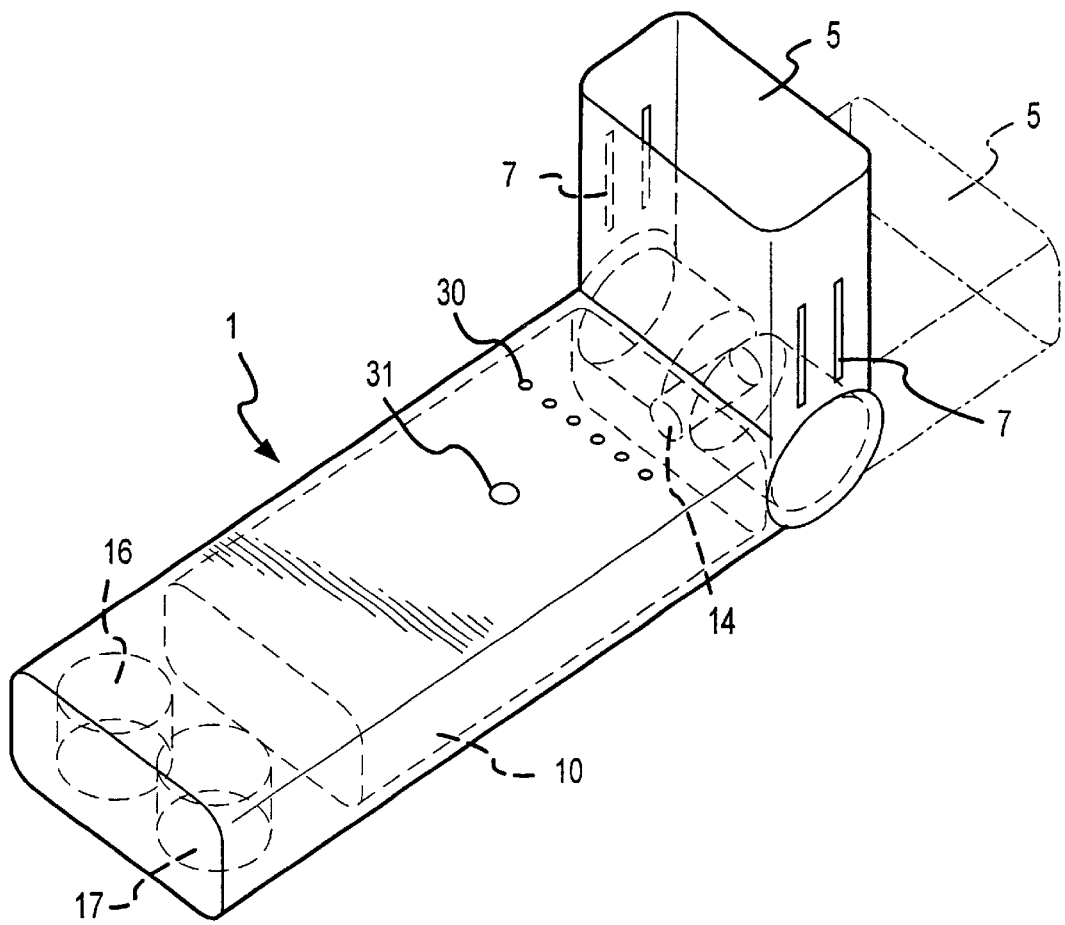
FIG. 4 is a schematic perspective view of a second embodiment of the invention.

A further difference is that in the embodiment of FIG. 4 the mouthpiece portion 5 is moveable hingedly between a storage position "A" in which it is in alignment with the body (shown in ghost outline in FIG. 4) and an active position "B" in which it is inclined at an angle to the body portion.

The mouthpiece may swivel about a swivel pin and the swivel motion may itself actuate an on/off switch to energize the controller 16.

If desired the apparatus may be provided with manual actuation (e.g. a push-button switch, not illustrated) instead of a pressure-sensitive switch, to control the operation and initiate an "actuation" signal.

In cigarette substitute apparatus according to FIG. 1, droplet sizes of the order of 1–20 micron diameter or more are acceptable. For pulmonary administration of drugs a small droplet size 1–5 micron diameter is preferred. For practical purposes droplets of below 10 micron diameter and more preferably of below 5 micron diameter are therefore preferred. If necessary, droplet size can be reduced after ejection from the dispenser-head by directing droplets at each other or at a suitable target designed to further fragment the droplets, or by injecting the droplets into an inhaled stream in a suitable manner. Optionally heating devices can be employed to vaporize the flowable substance and reduce droplet size.

Suitable drugs for delivery by the inhaler described include, by way of example only, analgesics, peptides and proteins. Other suitable agents include (i) $B_2$-bronchodilators—salbutamol, terbutaline sulphate, fenoterol hydrobromide, pirbuterol, reproterol hydrochloride, rimiterol hydrobromide, salmeterol (used extensively for treatment of acute asthma attacks and in prophylactic asthma therapy).

(ii) Antimuscarinic bronchodilators—Ipratropium bromide, oxitropium bromide (used in management of chronic bronchitis).

(iii) Corticosteroids—beclomethasone dipropionate, budesonide: used in prophylactic asthma therapy.

(iv) Sodium chromoglycate, nedocromil sodium (used in prophylactic asthma therapy). Antibiotic Therapy:

(v) Pentamidine isethionate—(antibiotic for the prophylaxis and treatment of pneumonia due to Pneumocystis carinii, a common secondary infection in HIV/AIDS patients).

Local Action (vi) Range of proprietary 'Over the Counter' nasal decongestant sprays for common cold symptoms, (vii) Corticosteroids—beclomethasone dipropionate, betamethasone sodium phosphate, budesonide, fluticasone propionate (used in prophylaxis and treatment of allergic rhinitis).

(viii) Sodium chromoglycate (used in prophylaxis of allergic rhinitis).

(ix) Anti-infective agents—e.g. dexamethasone, fusafungine, chlorhexadine hydrochloride (used in treatment of infection due to nasal staphylococci).

Systemic Action (x) Nasal administration of peptides related to antidiuretic hormone—desmopressin, lypressin (used in management of diabetes insipidus).

The apparatus for use in dispensing certain drugs may comprise programmed control means which issues a predetermined dose into each of a plurality of successive inhalations and in that case may be provided with a "dose complete" signal for example via LED 31 to indicate to a user when a full dose has been dispensed. The dose can be varied according to the composition being dispensed and the prescription for each user.

Figure 5:
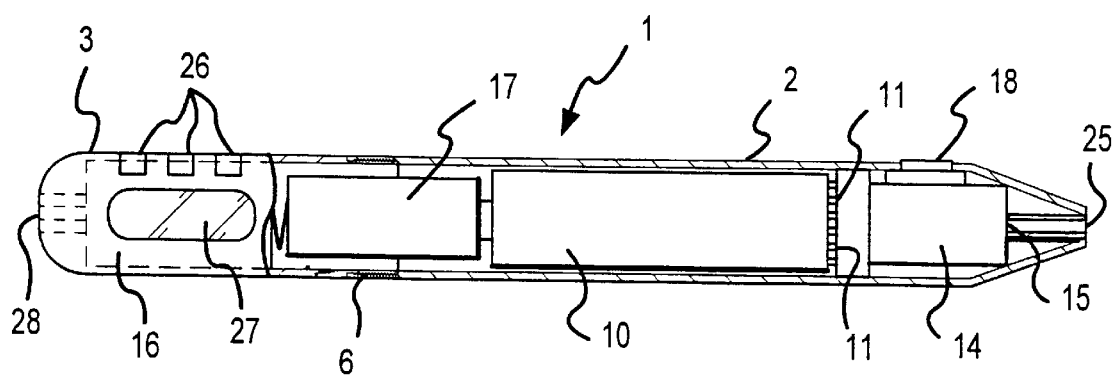
FIG. 5 is a schematic diagram of a third embodiment of the invention.

With reference to FIG. 5, there is shown a further embodiment of the invention which is adapted to dispense an active substance such as an anaesthetic, antiseptic or a liquid medication by topical application rather than by inhalation.

In surgery or medical treatment it is sometimes necessary to apply an anaesthetic, antiseptic or other fluid over a local area by means of an aerosol sprayed from a pressurized container. However it is difficult to control the amount and location of spray application. Moreover the use of CFC propellant as used in the aerosol is environmentally undesirable.

Parts of FIG. 5 corresponding in function to parts in the embodiment of FIG. 1 are identified by the same numerals.

With reference to FIG. 5 there is shown a dispenser comprising a pen shaped hollow tubular body 1 assembled from hollow body parts 2, 3. Body part 2 has a nozzle opening 25 at one end while body part 3 is closed at the end remote from nozzle opening 25. Body parts 2, 3 are separable connected at 6, for example by inter-engaging thread formations. A container 10 is situated within body 1 and contains a flowable substance. Container 10 is in fluid connection with one or more dispenser-heads 14 via one or more conduits. In the present example dispenser-head 14 is a piezoelectric crystal device such as used in an ink jet print head. Dispenser-head 14 can be energized from a battery 17 via an "on/off" control switch 18 adapted for finger operation while the dispenser is hand held. For example the dispenser may be held between thumb and middle finger and may carry a push button switch 18 which is operable by the first finger. In the embodiment of FIG. 5 when control switch 18 is actuated, dispenser-head 14 delivers flowable substance from container 10 through dispensing nozzles 15 as a spray of droplets directed outwardly from the dispenser via nozzle opening 25. The duration of the spray of droplets is determined by whether the control switch 18 is "on" or "off".

In a more highly preferred embodiment of the invention the volume of flowable substance sprayed as droplets per unit time can also be controlled. For example, the dispenser 1 is provided with one or more switches 26 (for example touch pad switches) which condition controller 16 (for example a microprocessor circuit) which in turn controls the amount of flowable substance being dispensed through dispensing nozzles 15 of dispenser-head 14 from which droplets are emitted and/or which controls the repetition rate of the dispenser-head 14 and thus the number of droplets delivered in a unit of time. Thus the droplet spray rate may be selectively light or heavy depending on the number of dispensing nozzles 15 emitting droplets and depending on the repetition rate of droplet emission.

If the dispenser-head 14 is provided with a plurality of dispensing nozzles 15 which are directed at preselected angles to the axis of the body, droplets of flowable substance may be directed in the axial direction or selectively at predetermined angles to the axial direction by controller actuation of a selected dispensing nozzle 15, or a selected combination of dispensing nozzles 15. In this manner a spray pattern of droplets may be selected by means of a suitable finger control of one or a number of switches 26 forming part of the microelectronic circuit of controller 16. If all dispensing nozzles 15 are directed axially the spray pattern may be made selectively narrow or broad.

Alternatively switches 26 may be adapted to select between a number of predetermined total dose dispensations or an additional controller may be provided to select total dose. In such manner, if the dispenser contains for example a liquid local anaesthetic, a surgeon can select a preset quantity and spray pattern of local anaesthetic to be applied during surgery. The surgeon could thus select between application of a small, medium or large dose, at each actuation of a switch 26 and could preselect between a narrow, medium, or broad spray pattern.

If desired the controller 16 may be provided with means to prevent inadvertent excessive use, for example by limiting the maximum dose of dispensed flowable substance which can be applied within a pre-specified time period.

Also, if desired, the control circuit can be provided with security locking which overrides the "on/off" switch. For example the device might be provided with a programmable security code and might be incapable of issuing its contents unless and until a corresponding code is entered by an intending user.

For this purpose the device may have a plug 28, socket or electronic transmitter/receiver which permits the device to interface with an external computer. The external computer might then also record data indicative of use, doses issued, user identification, patient identification, or similar data. The external computer may also re-enter new data in one or more memories in the controller of the device for example dose values, time parameters, security codes. This data is then used in controlling response of the device to actuation by the user.

Other forms of hand control, for example touch sensitive switches or rotary switches may be employed instead of switches 26.

Controller 16 may utilize digital or analogue control and may employ a microprocessor, or discrete circuit components. In preferred embodiments the circuit includes electronic memory, preferably of a type which is not erased due to lack of battery power. The circuit further desirably includes a display screen such as a single line LCD 27. The circuit may also employ a clock and be able to utilize and display date and time data and may have a key pad or equivalent input device or may rely for input upon communication with an external key pad. The LCD could be used to display data such as number of remaining doses or time and date of last dose.

Although the embodiment of FIG. 5 has been described with reference to dispensation of a flowable substance it will be appreciated that the material to be dispensed can be in the form of a gel, colloid, powder suspension or any other form suitable for dispensation via the dispenser-head 14.

In a further embodiment of the invention (not illustrated) the dispenser head is provided with a plurality of cartridges or chambers each adapted to contain a respective medication in flowable substance or solution form. Controller 16 may be programmed to provide an alarm (for example a beeper or flashing LED) at predetermined times or at predetermined times and dates. On next actuation of the device, it then delivers a predetermined dose of one medication or a combination or succession of medications each in a respective predetermined dose.

This embodiment is thus ideally suited for pre-programmed treatment of persons suffering from dementia or the like and for persons having to take a number of different medications each according to a schedule and who find self-administration confusing.

The device itself prompts the user to accept a dose and issues the appropriate doses of prescribed medication.

As will be apparent to those skilled in the art, features described in relation to one of the described embodiments may be combined with those of another.

Although the control signals have been described as pulses, those skilled in the art will appreciate that the signals can take a great variety of forms and may employ voltage or current signals, AC or DC signals, digital or analogue signals or the like, as required for operation of the dispenser-head selected. It is not necessary literally to count signals to eject a predetermined number of droplets and it will be understood that such expediencies as issuing "eject" signals at a predetermined frequency for a selected time interval are considered equivalent and within the scope hereof. Although the invention has been described in terms of electronic devices, fluidic devices and non electronic means of control may be employed.

Those skilled in the art will appreciate that with many dispenser-heads a principal ejected droplet sometimes has trailing satellite droplets which are very much smaller. References herein to a predetermined number of droplets refer to the number of principal droplets ejected, but if necessary the dispenser-head can be calibrated to issue a desired dose taking account of satellite drops without departing from the inventive concept hereof. Likewise it will be understood that the control of flowable substance viscosity is important and that therefore the volume of one substance issued in response to a given set of "eject" signals will not necessarily be the same as for another substance. However those skilled in the art will have no difficulty based on the teaching hereof in programming devices according to the invention to take account of these factors.

In another embodiment of the invention, a drop-on-demand type dispenser-head is employed that utilizes the distortion of a piezoelectric material to eject flowable substance and includes an array of channels in which the individual channels of the array each have side walls formed at least, in part, of a piezoelectric material. The channels are micron sized and are arranged such that the spacing between adjacent channels is relatively small. In the operation of this type of dispenser-head, flowable substance is directed to and resides in the channels until selectively ejected therefrom. Ejection of flowable substance from selected channels is effected due to the electromechanical nature of the piezoelectric side walls of the channels. Because piezoelectric material deforms when an electric field is applied there across, the side walls of selective channels deform by applying an electric field across select ones thereof. The electric field may be so selectively applied by digital or other means. This deformation of side walls of selected channels reduces the volume of the respective channels creating a pressure pulse in the flowable substance residing in those channels. The resultant pressure pulse then causes the ejection of a droplet of flowable substance from the front end of the particular channel adjacent the side walls across which the electric field is applied. The channels provide a correct delivery volume that is difficult to achieve in a single channel. Additionally, multiple channels give access to more volume of flowable substance in a shorter period of time.

Figure 6:
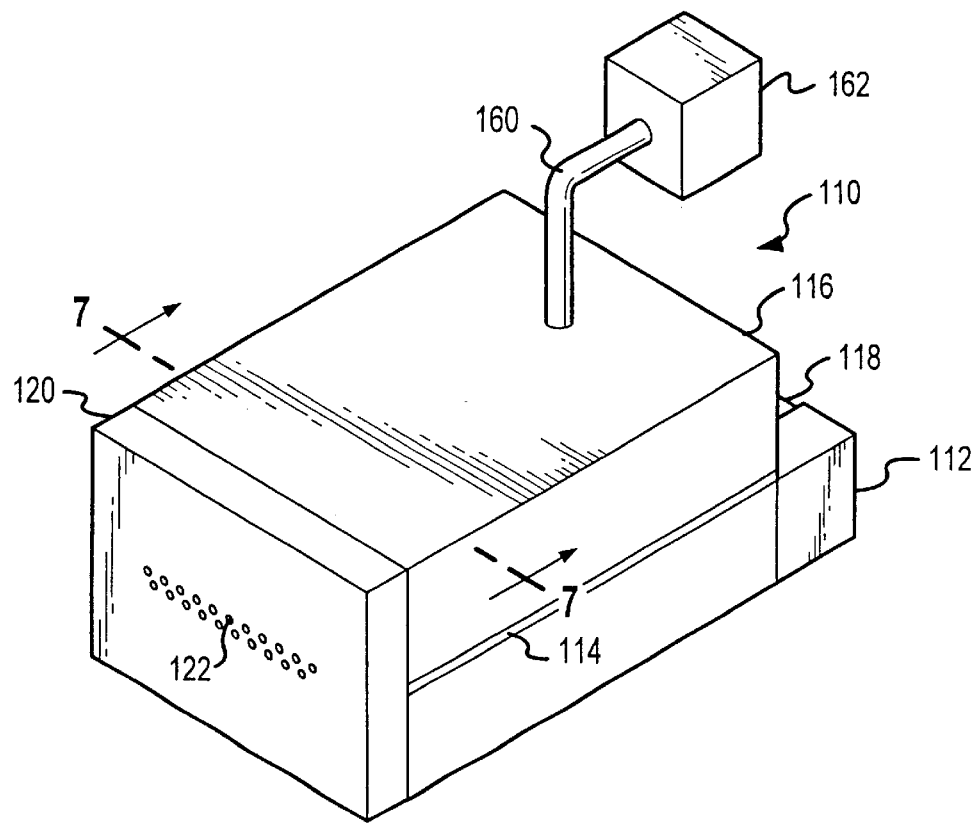
FIG. 6 is a perspective view of a schematically illustrated piezoelectric dispenser-head.

As shown in FIG. 6, the dispenser-head 110 includes a main body portion 112 which is aligned, mated and bonded to an intermediate body portion 114 which, in turn, is aligned, mated and bonded to a top body portion 116.

A plurality of vertical grooves of predetermined width and depth are formed through the intermediate body portion 114 and the main body portion 112 to form a plurality of pressure chambers or channels 118 (not visible in FIG. 6), thereby providing a channel array forming the dispenser-head 110. In conventional manner, channels 118 are in fluid connection to an inlet port 160 and fluid container 162.

The dispenser-lead 110 further includes a front wall 120 having a plurality of dispensing nozzles 122 extending therethrough. Each dispensing nozzle 122 is in fluid connection with a corresponding one of the plurality of channels 118, thereby providing droplet dispensing nozzles for dispenser-head 110.

Figure 7:
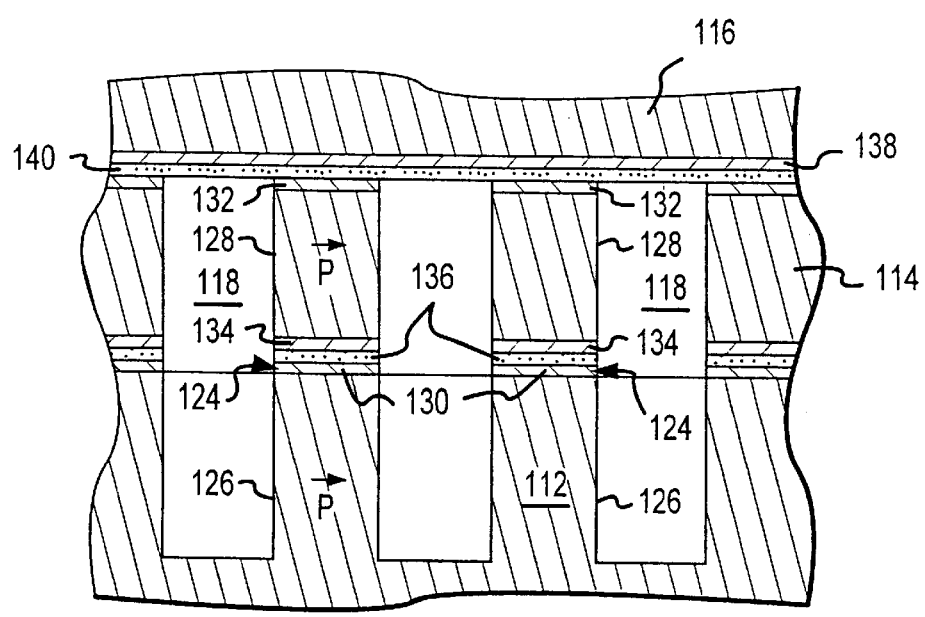
FIG. 7 is an enlarged partial cross-sectional view of the dispenser-head of FIG. 6 taken along line 7—7 illustrating a parallel channel array of the dispenser-head.

FIG. 7 shows an enlarged partial cross-sectional view of dispenser-head. 110 taken along line 7—7 of FIG. 6. Dispenser-head 110 includes a plurality of parallel spaced channels 118. Each channel 118 extends vertically from top body portion 116, along intermediate body portion 114 and part of main body portion 112 and extends lengthwise through dispenser-head 110. Main body portion 112 may be constructed of inactive or active material such as unpolarized or poled piezoelectric material. Top body portion 116 may be constructed of an inactive material such as unpolarized piezoelectric material.

Separating adjacent channels 118 are sidewall actuators 124, each of which include a first sidewall section 126 and a second sidewall section 128. First sidewall section 126 may be constructed of an inactive or active material such as for an unpolarized or poled piezoelectric material. In one embodiment, first sidewall section 126 is integrally formed with body portion 112. When first sidewall section 126 is constructed of an active poled piezoelectric material, it may be formed of lead zirconate titanate (PZT), polarized in direction "P" perpendicular to channels 118. Second sidewall section 128, is formed of an active material such as lead zirconate titanate (PZT) and polarized in direction "P" perpendicular to channels 118.

Mounted to the top side of each first sidewall section 126 is a metallized conductive surface 130 which can be a strip of metal. Similarly, metallized conductive surfaces 132 and 134, also formed of a strip of metal, are mounted to the top and bottom sides, respectively, of each second sidewall section 128. A first layer of a conductive adhesive 136 is provided to conductively attach metallized conductive surface 130, mounted to first sidewall section 126, and metallized conductive surface 134, mounted to second sidewall section 128. Conductive adhesive 136 can be an epoxy. Finally, the bottom side of top body portion 116 is provided with a metallized conductive surface 138. Metallized conductive surface 138 is mounted to metallized conductive surface 132 of second sidewall section 128 by a second layer of a conductive adhesive 140. In this manner, a series of channels 118, each channel being defined by the piezoelectric material of main body portion 112 along its bottom, the layer of conductive adhesive 140 along its top and a pair of sidewall actuators 124 is provided. Each sidewall actuator 124 is shared between adjacent channels 118.

A passivation coating may be applied to all exposed metallized conductive surfaces. In one embodiment, the metallized surfaces in dispenser-head 110 are electropolished prior to the deposition of passivation coatings. Dispenser-head 110 is placed in an acid bath and a voltage supply is attached to dispenser-head 110 in a manner to make the exposed metallized surfaces into the anode. When the voltage supply is energized, a slight amount of the metal of the metallized surfaces, such as surfaces 130 and 134, is removed or etched at the fluid interface which does not degrade the performance of dispenser-head 110. This minimizes the amount of exposed metal to be coated by the passivation coatings.

In an embodiment referring to FIG. 6, front wall 120 is a porous membrane and droplets may be created by forcing a flowable substance through the pores of the porous membrane. In a further embodiment the porous membrane is positioned adjacent to the dispensing nozzles 122 of dispenser-heads 110. Membrane 120 has pores of sufficient size and in sufficient numbers such that when the flowable substance is forced against membrane 120 by the dispenser-head 110 the flowable substance is aerosolized and droplets suitable for inhalation are created. In one embodiment, membrane pores have a size in the range of about 0.25 to 2.5 microns. When the pores have this size the particles which escape through the pores to create the aerosol have a diameter in the range of 0.5 to 5 microns.

Droplets may be released with an air flow intended to keep the particles within this size range. The creation of small particles may be facilitated by the use of a vibration device such as the piezoelectric dispenser-head described in FIG. 6, which provides a vibration frequency in the range of about 800 to about 4000 kilohertz. Those skilled in the art will recognize that some adjustments can be made in the parameters such as the size of the pores from which fluidic medium is released, vibration frequency, pressure, and other parameters based on the density and viscosity of the formulation to be aerosolized particles having a diameter in the range of about 0.5 to 20 microns.

Membrane 120 may include pores which have a diameter in the range of about 0.25 micron to about 6 microns and a pore density in the range of $1 \times 10^4$ to about $1 \times 10^8$ pores per square centimeter. Membrane 120 may be made of material having a density in the range of about 0.25 to 3.0 mg/cm$^2$, more preferably about 1.7 mg/cm sup 2, and with a thickness of about 2 to about 20 microns, more preferably 8 to 12 microns. Alternatively, membrane 120 can be an area of pores with a diameter in the range of 0.25 micron to about 6 microns; which pores are positioned over the area of about 1 sq. mm. to about 1 sq. cm.; and which area contains from 10 to 10,000 pores.

The material of the membrane has sufficient structural integrity so that it is maintained intact (will not rupture) when the material is subjected to force sufficient to aerosolize the flowable substance. That force can be in range of 20 to about 200 psi while flowable substance is forced through the pores of membrane 14.

Membrane 120 can be made of a hydrophobic material including but not limited to polycarbonates, polyesters, and the like, with the pores being formed by anisotropic etching, etching through a thin film, and the like. The membrane material can include pores of different geometric configurations including but not limited to cylinders, non-cylinders, spherical, non-spherical, hour-glass, conical, square, rectangular and irregular shapes. When a conical configuration is used it is designed with the narrowest point of the conical configuration having an opening with a diameter in the range of 0.2 micron to 6 microns.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An inhaler, comprising:

an inhaler housing;

a mouthpiece interconnected with said inhaler housing;

a flowable substance container associated with said inhaler housing;

a droplet ejection device fluidly interconnected with said flowable substance container, wherein said droplet ejection device comprises a plurality of droplet ejection orifices and a plurality of droplet ejection actuators which are independently actuatable;

a programmable controller operatively interconnected with said droplet ejection device; and a heating means disposed within said inhaler housing.

2. An inhaler, as claimed in claim 1, wherein:

said inhaler housing comprises first and second ends, wherein said mouthpiece is disposed on said first end wherein said second end is closed.

3. An inhaler, as claimed in claim 1, wherein:

said inhaler housing comprises a plurality of air inlet slots.

4. An inhaler, as claimed in claim 3, wherein:

said inhaler housing comprises first and second ends and a sidewall extending therebetween, wherein said air inlet slots are disposed on said sidewall.

5. An inhaler, as claimed in claim 3, wherein:

said inhaler housing comprises a central, longitudinal axis, wherein said air inlet slots are disposed parallel to said central, longitudinal axis.

6. An inhaler, as claimed in claim 3, further comprising:

means for controlling airflow through said air inlet slots.

7. An inhaler, as claimed in claim 1, wherein:

said inhaler housing comprises first and second ends with a sidewall extending therebetween, wherein said mouthpiece is disposed on said first end and defines an exit from said inhaler housing, wherein said second end is closed, and wherein said inhaler housing comprises a plurality of air inlet slots disposed on said sidewall and which define an inlet to said inhaler housing.

8. An inhaler, as claimed in claim 1, wherein:

said inhaler housing comprises first and second housing sections which are detachably interconnected, wherein said flowable substance container is disposed within said inhaler housing and may be accessed by separating said first housing from said second housing.

9. An inhaler, as claimed in claim 1, wherein:

said flowable substance container comprises a protective cartridge and a collapsible bladder disposed within said protective cartridge.

10. An inhaler, as claimed in claim 1, wherein:

said flowable substance container is disposable and may be replaced by another said flowable substance container.

11. An inhaler, as claimed in claim 1, wherein:

said flowable substance container is disposed within said inhaler housing.

12. An inhaler, as claimed in claim 1, wherein:

at least some of said plurality of droplet ejection orifices have different diameters.

13. An inhaler, as claimed in claim 1, wherein:

at least some of said plurality of droplet ejection orifices are disposed in different orientations.

14. An inhaler, as claimed in claim 1, wherein:

said heating means is disposed between said droplet ejection device and said mouthpiece.

15. An inhaler, as claimed in claim 1, wherein:

said heating means comprises means for increasing a temperature of droplets ejected from said droplet ejection device.

16. An inhaler, as claimed in claim 1, wherein:

said heating means comprises means for reducing a size of droplets ejected from said droplet ejection device.

17. An inhaler, as claimed in claim 1, wherein:

said controller comprises a programmable logic circuit.

18. An inhaler, as claimed in claim 1, wherein:

said controller comprises a microprocessor.

19. An inhaler, as claimed in claim 1, wherein:

said controller comprises means for controlling a quantity of a flowable substance ejected from said flowable substance container by said droplet ejection device.

20. An inhaler, as claimed in claim 1, further comprising:

an inhalation sensor associated with said inhaler housing and operatively interconnected with said controller.

21. An inhaler, as claimed in claim 1, wherein:

said controller comprises means for sending a dose signal to said droplet ejection device.

22. An inhaler, as claimed in claim 21, wherein:

said dose signal comprises a set of eject signals.

23. An inhaler, as claimed in claim 21, wherein:

said dose signal comprises a train of voltage pulses.

24. An inhaler, as claimed in claim 21, wherein:

said dose signal comprises a train of pulses directed serially to one of said droplet ejection actuators.

25. An inhaler, as claimed in claim 21, wherein:

said dose signal comprises a sequence of pulses directed in parallel to a plurality of said droplet ejection actuators.

26. An inhaler, as claimed in claim 1, wherein:

said controller comprises means for programming said controller to address specific said droplet ejection actuators so as to eject droplets of a flowable substance from selected said droplet ejection orifices.

27. An inhaler, as claimed in claim 1, wherein:

said controller comprises means for controlling a pulse spacing, pulse width, and pulse frequency of a dose signal sent to said droplet ejection device by said controller.

28. An inhaler, as claimed in claim 1, wherein:

said controller comprises means for controlling a time interval during which droplets of a flowable substance are discharged from said droplet ejection device.

29. An inhaler, as claimed in claim 1, wherein:

said controller comprises means for providing a dose complete signal which indicates to a user of said inhaler that a full dose has been dispensed.

30. An inhaler, as claimed in claim 1, wherein:

said controller comprises means for preventing inadvertent, excessive use of said inhaler.

31. An inhaler, as claimed in claim 1, wherein:

said controller comprises means for limiting a maximum dose of a flowable substance from said flowable substance container which can be discharged from said inhaler within a predetermined time period.

32. An inhaler, as claimed in claim 1, wherein:

said controller comprises means for locking said inhaler.

33. An inhaler as claimed in claim 32, wherein:

said means for locking comprises a security code.

34. An inhaler, as claimed in claim 1, wherein:

said controller comprises means for providing an alarm schedule whereby an alarm will be activated in accordance with said alarm schedule.

35. An inhaler, as claimed in claim 1, wherein:

said controller comprises a microprocessor, electronic memory, clocks, power supply, and sensors.

36. An inhaler, as claimed in claim 1, further comprising:

a battery operatively interconnected with said controller.

37. An inhaler, as claimed in claim 36, wherein:

said battery is disposed within said inhaler housing.

38. A method for delivering droplets of a flowable substance from an inhaler to a patient, wherein said inhaler comprises a controller which is operatively interconnected with a droplet ejection device, wherein said droplet ejection device comprises a plurality of droplet ejection orifices and a plurality of droplet ejection actuators, and wherein said method comprises the steps of:

providing said flowable substance to said droplet ejection device;

executing a first programming step which comprises programming a controller which is operatively interconnected with said droplet ejection device, wherein said programming step comprises selecting which of said droplet ejection actuators should receive a first dose signal from said controller;

directing said first dose signal to each of said droplet ejection actuators from said selecting step;

discharging said flowable substance through said droplet ejection orifices associated with said droplet ejection actuators from said selecting step;

generating droplets of said flowable substance from said discharging step; and inhaling said droplets provided by said generating step.

39. A method, as claimed in claim 38, wherein:

said executing a first programming step comprises operatively interconnecting said inhaler with an external computer.

40. A method, as claimed in claim 38, further comprising the steps of:

executing a second programming step comprising programming said controller which is operatively interconnected with said droplet ejection device and which comprises selecting which of said droplet ejection actuators should receive a second dose signal from said controller, wherein a combination of said droplet ejection actuators from said selecting step of said executing a first programming step are different from a combination of said droplet ejection actuators from said selecting step of said executing a second programming step.

41. A method, as claimed in claim 38, wherein:

said selecting step comprises selecting a single said droplet ejection actuator to receive said first dose signal from said controller.

42. A method, as claimed in claim 38, wherein:

said directing step comprises directing a set of ejection signals.

43. A method, as claimed in claim 38, wherein:

said directing step comprises directing a train of voltage pulses.

44. A method, as claimed in claim 38, wherein:

said directing step comprises directing a train of pulses serially to one of said droplet ejection actuators.

45. A method, as claimed in claim 38, wherein:

said directing step comprises directing a sequence of pulses in parallel to a plurality of said droplet ejection actuators.

46. A method, as claimed in claim 38, wherein:

said directing step comprises directing a sequence of pulses, wherein said programming step comprises programming a pulse spacing, a pulse width, and pulse frequency of said sequence of pulses.

47. A method, as claimed in claim 38, further comprising the step of:

heating said droplets after said generating step and before said inhaling step.

48. A method, as claimed in claim 47, wherein:

said heating step comprises affecting a temperature of said droplets.

49. A method, as claimed in claim 47, wherein:

said heating step comprises reducing a size of said droplets.

50. A method, as claimed in claim 38, further comprising the step of:

providing a resistance to said inhaling step.

51. A method, as claimed in claim 38, further comprising the step of:

providing a dose complete signal to said patient after a full dose has been dispensed from said inhaler.

* * * * *